United States Patent [19]

Dasgupta

[11] Patent Number: 5,660,703
[45] Date of Patent: Aug. 26, 1997

[54] APPARATUS FOR CAPILLARY ELECTROPHORESIS HAVING AN AUXILIARY ELECTROOSMOTIC PUMP

[75] Inventor: Purnendu K. Dasgupta, Lubbock, Tex.

[73] Assignee: The Dow Chemical Company, Midland, Mich.

[21] Appl. No.: 455,579

[22] Filed: May 31, 1995

[51] Int. Cl.$^6$ .................... G01N 27/26; G01N 27/447
[52] U.S. Cl. ................ 204/601; 204/603; 204/604; 417/49; 417/50
[58] Field of Search ................ 204/299 R, 601, 204/603, 604; 417/50, 49

[56] References Cited

U.S. PATENT DOCUMENTS

| | | | |
|---|---|---|---|
| 3,649,499 | 3/1972 | Virtanen et al. | 204/108 |
| 4,459,198 | 7/1984 | Mizuno et al. | 204/299 R |
| 5,092,972 | 3/1992 | Ghowsi | 204/182.1 |
| 5,169,510 | 12/1992 | Lunte et al. | 204/299 R |
| 5,181,999 | 1/1993 | Wiktorowicz | 204/180.1 |
| 5,320,730 | 6/1994 | Ewing et al. | 204/299 R |
| 5,322,607 | 6/1994 | Baer et al. | 204/299 R |
| 5,358,612 | 10/1994 | Dasgupta et al. | 204/180.1 |
| 5,358,618 | 10/1994 | Ewing et al. | 204/299 R |

OTHER PUBLICATIONS

Dasgupta et al., "Electroosmosis: A reliable fluid propulsion system for flow injection Analysis" (Jun. 1994) pp. 1792–1798, Abstract printed Apr. 15, 1994.

Dasgupta, et al., Auxiliary Electroosmotic Pumping in Capillary Electrophoresis, Anal. Chem., vol. 66, No. 19, pp. 3060–3065 Oct. 1994.

Dasgupta, et al., Suppressed Conductometric Capillary Electrophoresis Separation Systems, Anal.Chem., vol. 65, pp. 1003–1011 Apr. 1993.

Dasgupta, et al., Electroosmosis: A reliable Fluid Propulsion System for Flow Injection Analysis, Anal. Chem., vol. 66, pp. 1792–1798 Jun. 1994.

Jorgenson, et al., Zone Electrophoresis in Open–Tubular Glass Capillaries, Anal. Chem, 53, pp. 1298–1302 Jul. 1981.

O'Shea, et al., Capillary electrophoresis with electrical chemical detection employing an on–column Nafion joint, J. of Chrom., 593, 1992, pp. 305–312. (no month).

Kok, Off–Column Detection with Pressure Compensation in Capillary Electrophoresis, Anal. Chem, 65, 1853–1860 Jul. 1993.

Jorgenson, et al., Science, Capillary Zone Electrophoresis, vol. 222, pp. 266–272 Oct. 1983.

Hayes, et al., Electroosmotic Flow Control and Surface Conductance in Capillary Zone Electrophoresis, American Chem. Soc., 65, pp. 2010–2013 Aug. 1993.

Datta, et al., Electrokinetic Dispersion in Capillary Electrophoresis, AIChE, vol. 36, No. 6, vol. 36, pp. 916–926 Jun. 1990.

Grushka, Effect of hydrostatic flow on the efficiency in capillay electrophoresis, Journal of Chromatography, 1991, 559, pp. 81–93. (no month).

*Primary Examiner*—Arun S. Phasge
*Attorney, Agent, or Firm*—Linda Blair Meier

[57] ABSTRACT

Apparatus for capillary electrophoresis having an auxiliary electroosmotic pump. Following a conventional capillary electrophoresis system having a single power supply, a separation capillary, and an optical detector, a conductive membrane connects a second capillary to a second power supply. The second capillary and second power supply act together as an auxiliary electroosmotic pump capable of augmenting or inhibiting the bulk electroosmotic flow in the separation capillary. The apparatus can be used to optimize the stacking profile of the sample and, thus, improve the separation efficiencies for charged solutes.

1 Claim, 1 Drawing Sheet

APPARATUS FOR CAPILLARY ELECTROPHORESIS HAVING AN AUXILIARY ELECTROOSMOTIC PUMP

BACKGROUND OF THE INVENTION

Electrophoresis is a well developed chemical analysis technique. A review reference on this subject is Chapter 9 of Chromatography-Fundamentals and Applications of Chromatographic and Electrophoretic Methods, Part A: Fundamentals and Techniques, edited by E. Heftmann, Elsevier Scientific Publishing Company, 1983, herein fully incorporated by reference. Capillary electrophoresis (CE) is an important advance in electrophoresis which was pioneered by Jorgenson and Lukacs as reported in *Analytical Chemistry*, 53, 1298–1302 (1981) and in *Science* 222, 266–272 (1983), each of which are herein fully incorporated by reference.

In capillary electrophoresis, the electrophoretic movement of a charged analyte species is augmented or inhibited by the bulk electroosmotic flow (EOF) of the electrolyte medium. In conventional systems, both electrophoretic and electroosmotic movement results from the same applied voltage and cannot be independently controlled.

In most CE applications, some degree of stacking occurs. Stacking means that ionic solutes injected in the sample volume become concentrated in a lesser volume prior to separation. The shape of the concentrated sample plug after stacking controls the efficiency of the eventual separation of the sample constituents. For a cylindrical capillary, the ideal form is that of a cylindrical plug. The stacking process itself originates from a difference in the electric field between the sample zone, which is typically less conductive than the bulk electrolyte, and the bulk separation medium in the capillary. However, the EOF is also different between the sample zone and the bulk separation medium; this ensures that the sample will not be stacked as a perfectly cylindrical plug, but will be parabolically distorted at the front or rear edges.

In systems where detection preferably takes place outside the high electric field (as in suppressed conductivity detection and some types of electrochemical detection), flow in the post separation zone cannot be plug like. It has been reported that augmentation of EOF by a hydrostatic head or pressure minimizes the loss of separation efficiency in such systems. (See, for example, Kok, W. *Th. Anal. Chem.* 1993, 65, 1853–1860.)

A different approach to controlling EOF in a capillary is based on the magnitude of the EOF in a capillary being a function of the zeta potential of the capillary surface which can be manipulated by a second, radially applied, field. (See, for example, Ghowsi, U.S. Pat. No. 5,092,972.) The magnitude of the radial field can be maintained uniform across the length of the capillary using a resistive coating or a liquid medium surrounding the outer side of the separation capillary to uniformly dissipate the second field. The radial field can also be applied more simply through a conductive sheath; in this case, the radial field is not uniform across the capillary. In either case, little or no plate losses occur; a significant amount of additional work has been carried out to further develop the concept of a radially applied field in CE. (See, for example, Ewing, A. G. *Anal. Chem.* 1993, 65, 2010–2013.) The major drawback of the radial field application approach is that the degree of control that can be exercised over the EOF is highly pH dependent and can be very limited at pH values far removed from the $pK_a$ of the surface ionizable groups.

The art of capillary electrophoresis would be improved by an apparatus capable of controlling EOF with less dependence on pH and capable of performing CE analysis with minimized distortion of the sample plug.

SUMMARY OF THE INVENTION

The present invention is an apparatus for capillary electrophoresis that improves separation efficiency for charged solutes by using an auxiliary electroosmotic pump to counteract distortion in the shape of the sample plug which results from a difference in EOF between a sample zone and the bulk separation medium in the separation capillary.

The present invention is an apparatus for capillary electrophoresis, comprising: a first high voltage source; a first electrode being in electrical communication with the first high voltage source; a separation capillary having an inlet end and an outlet end, the inlet end being in electrical communication with the first electrode when the separation capillary is filled with an electrolyte solution which is in contact with the first electrode; a detector in fluid communication with the outlet end of the separation capillary; a grounding joint in fluid communication with the detector; a pumping capillary having a first end and a second end, the first end being in fluid communication with the grounding joint; a second electrode being in electrical communication with the second end of the pumping capillary when the pumping capillary is filled with an electrolyte solution which is in contact with the second electrode; and a second high voltage source being in electrical communication with the second electrode.

DETAILED DESCRIPTION OF THE INVENTION

Following a conventional capillary electrophoresis system having a single high voltage source, a separation capillary, and an optical detector, a grounding joint may be used to connect a second capillary to a second high voltage source. The grounding joint serves as a common ground for both high-voltage sources. The second high voltage source is used to cause electroosmotic flow in the second capillary which can act as an electroosmotic pump for the fluid in the CE separation capillary. The direction and magnitude of the electric field applied to the second capillary govern if the bulk flow in the first capillary is augmented, inhibited, or unaffected by the pumping action exerted by the second capillary.

Figure 1:
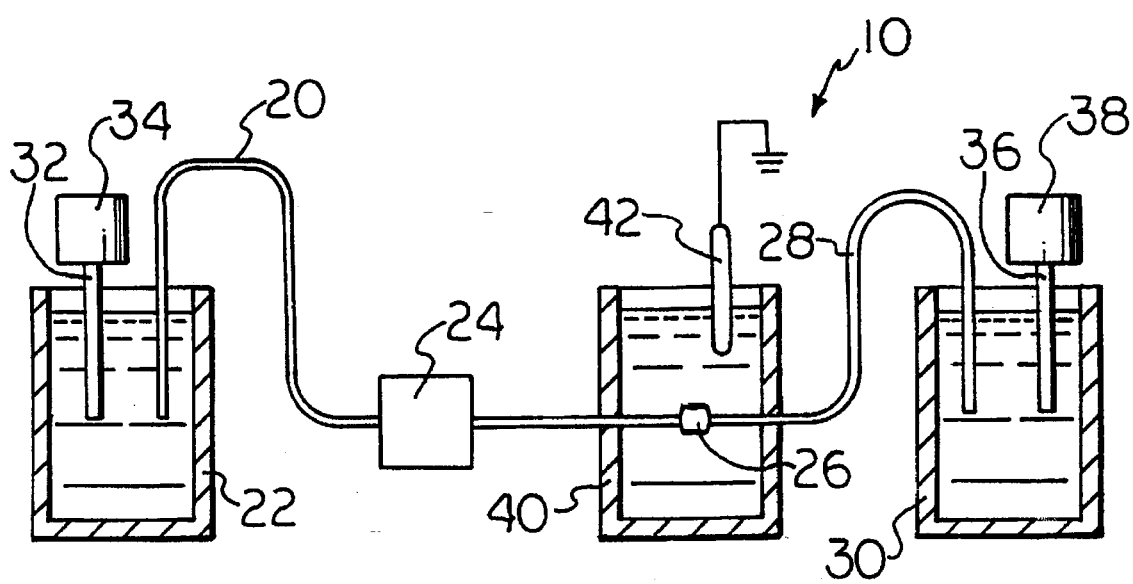
FIG. 1 is a schematic diagram of an apparatus embodiment of the present invention.

Referring now to FIG. 1, therein is shown an apparatus embodiment 10 of the invention which includes a separation capillary 20 having one end inserted into an electrolyte solution within source vial 22 and the other end connected to detector 24. Detector 24 is in turn in fluid communication with grounding joint 26, which is in fluid communication with one end of pumping capillary 28. The other end of pumping capillary 28 is inserted into an electrolyte solution within vial 30. Electrode 36, which is connected to high voltage supply 38, is also inserted into the electrolyte solution within vial 30. Similarly, electrode 32, which is connected to a separate high voltage supply 34, is inserted into the electrolyte solution within source vial 22.

Grounding joint 26 is positioned within container 40, which contains the same electrolyte contained in either source vial 22 or vial 30, such that grounding joint 26 is immersed in the electrolyte solution. All three containers 22, 30, 40 may contain the same electrolyte. A grounded electrode 42 is also positioned in the electrolyte solution in container 40. Joint 26 is the common ground for high voltage supplies 34 and 38. Other than the flow resistance posed by capillary 28, when high voltage supply 34 and high voltage supply 38 are opposed in sign, the EOF generated in capillary 28 generally augments the EOF in capillary 20. When the signs are the same, one flow generally inhibits the other.

A "separation capillary" is capillary in which components of a sample can be separated as is conventional in capillary electrophoresis. Preferably, the separation capillary is a silica capillary. As is well known in the art of capillary electrophoresis, an "electrolyte solution" is liquid solution containing a an electrolyte which can be flowed by electroosmosis.

The term "grounding joint", as used herein, refers to an electrically grounded joint which is capable of providing a hydraulic connection between two capillaries. Such grounding joints are commonly known in the art of capillary electrophoresis. Suitable grounding joints are described, for example, in U.S. Pat. No. 5,169,510 which is herein incorporated by reference.

As used herein, the term "pumping capillary" refers to a capillary capable of carrying an electrolyte solution which is to be pumped by electroosmosis. A pumping capillary can be made of materials such as many plastics and glasses, surface modified plastics and glasses, or columns filled with silica, clay, sponge, ion exchange resins, etc. Fused silica capillaries are preferred.

Using the present invention, there are at least two separate regions in which differences in electroosmotic flow velocities between the sample zone and the bulk electrolyte solution can be made to arise. The first is following sample introduction; the second is at the junction between the separation capillary 20 and the pumping capillary 28.

For the range of auxiliary electroosmotic pumping useful in the present context, the electrical analog of the present system is tantamount to a single high-voltage power supply connected across a potentiometer. The terminal ends of the potentiometer are connected to the terminal ends of the conjoined capillary system. The slider of the potentiometer, representing a floating ground, connects the conductive joint. The field strength in each segment can be deliberately varied. (The chemical composition of each segment could also be varied through a valving system as described, for example, in Dasgupta, P. K.; Liu, S. *Anal. Chem.* 1994, 66, 1792–1798.) If the distortion in the sample band shape brought about during electrostacking can be compensated for by introducing a compensating amount of distortion of the flow profile through auxiliary electroosmotic pumping, the overall efficiency should improve. In addition, auxiliary electroosmotic, rather than hydrostatic, pumping should be better suited for providing the necessary corrective action because it is the difference in electroosmotic flow velocities between the sample and the bulk electrolyte solution that is responsible for the distorted electrostacked band profile.

In the absence of a second capillary and a second electric field, the migration velocity ($u_m$) through the separation capillary in CE is:

$$u_m = E_1(\mu_{eo} + \mu_{ep})$$

wherein $E_1$ is the electric field on the separation capillary 20; $\mu_{eo}$ is the electroosmotic mobility; and $\mu_{ep}$ is the electrophoretic mobility. Using the apparatus of the present invention, the overall migration velocity ($u_m$) of the components in the electrolyte solution may be given by the vector sum of the overall electroosmotic velocity and the electrophoretic velocity, which results in the following equation:

$$u_m = \mu_{eo}(V_1 + V_2)/(L_1 + L_2) + E_1\mu_{ep}$$

wherein $V_1$ is the voltage applied on the $L_1$ centimeter long separation capillary 20; $V_2$ is the voltage applied on the $L_2$ centimeter long pumping capillary 28; $E_1$ is the electric field strength on the separation capillary 20 ($E_1 = V_1/L_1$); $\mu_{eo}$ is the electroosmotic mobility; and $\mu_{ep}$ is the electrophoretic mobility. It is assumed that capillaries 20 and 28 contain the same solution or solutions with the same electroosmotic mobility. Thus, voltage applied on the pump capillary 28 can dramatically affect the migration rate in the separation capillary 20. The change in migration behavior brought about by auxiliary pumping affects both peak efficiency and peak asymmetry. The reproducibility of auxiliary pumping attained with the present invention is as good as the reproducibility of EOF in a single capillary.

Figure 2:
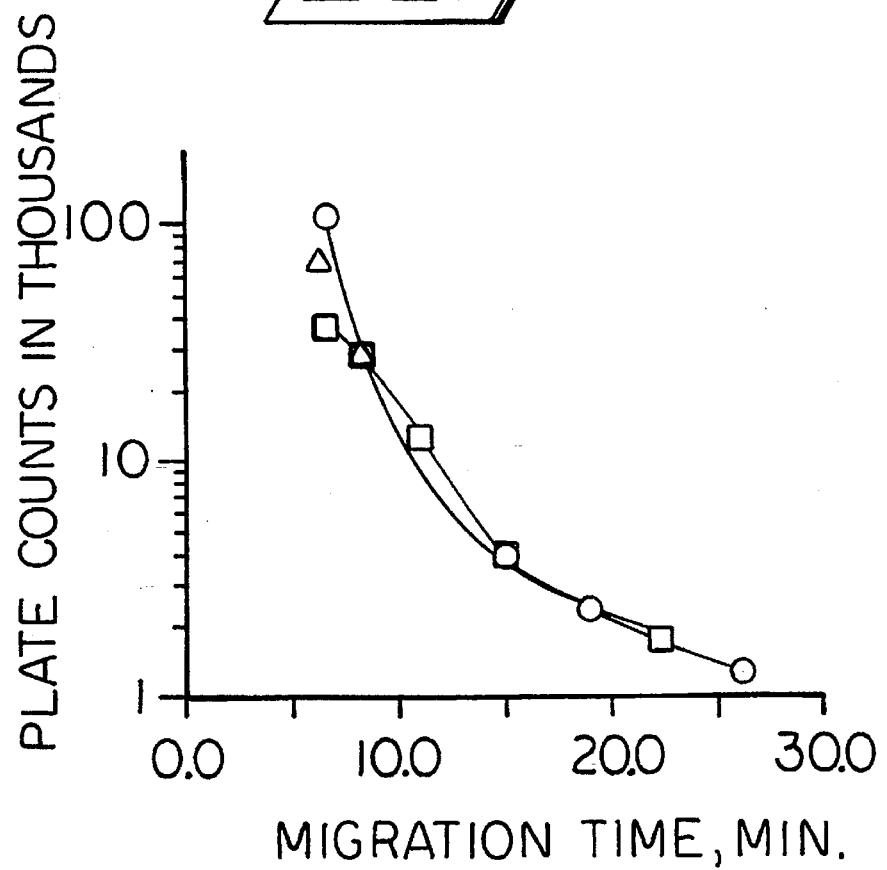
FIG. 2 is a graph showing change in peak efficiency as a function of auxiliary electroosmotic or hydrostatic pumping.

Referring now to FIG. 2, therein is shown a graph of plate counts (note the logarithmic ordinate) versus migration time. Data points obtained using auxiliary electroosmotic pumping are represented by circles and data points obtained using auxiliary hydrostatic pumping are represented by squares. The triangle represents a conventional single capillary result. The graph shows the change in peak efficiency as a function of auxiliary electroosmotic or hydrostatic pumping using an anionic solute. Tables 1 and 2 represent the data graphed in FIG. 2 for auxiliary electroosmotic pumping based on applied voltage, and for auxiliary hydrostatic pumping based on head height, respectively.

TABLE 1

| AUXILIARY ELECTROOSMOTIC PUMPING | | |
|---|---|---|
| MIGRATION TIME (min.) | PUMPING VOLTAGE APPLIED (kV) | PLATE COUNT |
| 6.5 | −5.7 | >100,000 |
| 8.5 | −3 | ~29,000 |
| 15.0 | 0 | ~4,000 |
| 19.0 | 0.6 | ~21,000 |
| 26.5 | 1.2 | ~1,500 |

TABLE 2

| AUXILIARY HYDROSTATIC PUMPING | | |
|---|---|---|
| MIGRATION TIME (min.) | HEAD HEIGHT (cm) | PLATE COUNT |
| 6.5 | 15 | ~38,000 |
| 8.5 | 10 | ~29,000 |
| 11.0 | 5 | ~13,000 |
| 15.0 | 0 | ~4,000 |
| 22.5 | −3 | ~2,000 |

The observed peak efficiency varies as the extent of auxiliary pumping is varied, whether induced hydrostatically or electroosmotically, and the peak efficiencies typically display a maximum. Using hydrostatic pumping superimposed on electroosmotic flow in a single capillary has been well studied both experimentally and theoretically (see, for example, Grushka, E. *J. Chromatogr.* 1991, 559, 81–93;

and Datta, R.; Kotamarthi, V. R. *AIChE J.* 1990, 36, 916–926); maximum plate counts are conventionally obtained when the hydrostatic potential is zero with a single capillary system.

For the conventional single capillary systems studied (neutral, anionic, and cationic solutes with corresponding electrolyte system), the maximum plate counts were reproducibly found to be within plus or minus 5 millimeters of zero hydrostatic head. For the experimental results shown in FIG. 2, the results with zero hydrostatic head and no hydrostatic resistance (single capillary system) correspond to about 65,000 plates (single triangle). If a second capillary is connected to the separation capillary, the latter presents some resistance to the flow, and the maximum number of plates is obtained with added hydrostatic potential, similar to the results reported by Kok, W. *Th. Anal. Chem.* 1993, 65, 1853–1860. Although there is a configurational difference between the experiments of Kok and those herein in that the hydrostatic resistance element is downstream from the detector, a hydrostatic backflow is nevertheless generated and the same considerations as those outlined by Kok hold. The maximum plate count obtained with an optimum amount of hydrostatic head is less than that when no flow resistance is present. For the experiment shown in FIG. 2, the maximum plate count obtained with auxiliary hydrostatic pumping is obtained with a hydrostatic head of ca. 20 centimeters and is less than 40,000 theoretical plates.

Under appropriate experimental conditions, the maximum plate count (peak efficiency) observed using auxiliary electroosmotic pumping may be greater than that obtained in a single capillary or using auxiliary hydrostatic pumping. The experimental results shown in FIG. 2 indicate in excess of 100,000 plates when the voltage applied by high voltage source 38 is about −5.7 kilovolts. In excess of 190,000 plates may be observed in the same experimental system when the voltage applied by high voltage source 38 is about −6 kilovolts where the mobility of the carrier electrolyte ion is matched with the anionic dye solute by incorporating 10 millimolar sodium anthraquinone-2-sulfonate in borax electrolyte.

EXAMPLES

Except as otherwise stated, separation capillary 20 is 40 cm in length and pumping capillary 28 is 20 cm in length. Both capillaries are fused silica (75 μm i.d., 375 μm o.d., Polymicro Technologies, Phoenix, Ariz.). A grounding joint 26 is made using a stretched piece of a NAFION 014 brand ion exchange tubing (Perma-Pure Products, Toms River, N.J.) which is swelled in methanol, slipped over the ends of capillaries 20 and 28, and tied in place firmly with nylon or Kevlar thread. For all of the present experiments, the same electrolyte is used in both capillaries 20 and 28 and is contained in each terminal vial 22 and 30. The grounding joint 26 is immersed in the same electrolyte contained in a separate vial 40 and serves as a common ground for two identical power supplies 34 and 38 (CZE 1000R, Spellman Inc., Plainview, N.Y.). Samples are introduced hydrostatically into the separation capillary 20, as is conventional in CE; typically, sample is introduced for 5 seconds, with a height difference of 10.5 centimeters between the inlet and outlet ends of the separation capillary.

The test analytes consist of (a) negatively charged (anionic) solutes, 40 micromolar concentration of sulfonephthalein dyes in 100 micromolar $Na_2B_4O_7$, pH~9, such as bromthymol blue (BTB), detected at 610 nanometers,; (b) an uncharged solute, benzyl alcohol (100 micromolar in water, detected at 208 nanometers); and (c) positively charged (cationic) solute, 500 micromolar $FeSO_4$ and 200 micromolar hydrazine sulfate (as an antioxidant) in 20 millimolar 1,10-phenanthroline (pH 6.1).

The carrier electrolyte for the anionic and neutral solute experiments is a 2 millimolar $Na_2B_4O_7$, pH 9.2 electrolyte and +9 kilovolts is applied on separation capillary 20. For the cationic solute experiment, the carrier electrolyte contains 20 millimolar, 1,10-phenanthroline, 20 millimolar $NBu_4ClO_4$, 2 millimolar $Na_2HPO_4$, and has a pH of 7.9. The EOF with this electrolyte is much less than with the borate, and from about +9 to +18 kilovolts is applied on separation capillary 20. In all three cases, the voltage applied on pump capillary 28 is varied both in sign and magnitude. Detector 24 is a LINEAR PHD (Thermo Separation Systems) equipped with a ball lens for capillary detection.

The apparent peak areas (the absorbance×time product) are related directly to the migration time, and are not constant as a function of the applied pump capillary voltage. Because the migration velocity varies, a constant value is obtained only when the apparent area is multiplied by the migration rate. The peak asymmetry does not change monotonically with the applied voltage.

In favorable cases, the use of auxiliary pumping can bring about large changes in the migration time. In the anionic solute case, the migration time changes from 1.7 minutes, with high voltage source 38 at −23 kilovolts, to greater than 20 minutes with high voltage source 38 at +1.7 kilovolts. With high voltage source 38 approaching +5 kilovolts, the analyte does not elute. This degree of bulk flow control is substantially larger than that attainable with radial field effects, especially at this operating pH.

Experimental results indicate that enhanced efficiencies arise as a result of changes in the band asymmetry brought about by the auxiliary electroosmotic flow. For an anionic solute where the sample is initially stacked with a reversed parabolic profile, optimum efficiency is observed with a field strength on the pump capillary 28 that is greater than that on the separation capillary 20; under these conditions, the pump capillary 28 should tend to impose a slight front parabolic correction to the separation capillary 20. Conversely, for a cationic solute where the sample is initially stacked with a forward parabolic profile, the optimum efficiency is observed at electric field strengths on the pump capillary 28 lower than that on the separation capillary 20; in this case, the overall magnitude of the electroosmotic flow is much lower and the observed range of optimum efficiency thus extends over a greater range of the applied pump capillary voltage.

Plate counts are computed from $N=5.54\ (t_m/W_{1/2})^2$ where $t_m$ is the migration time and $W_{1/2}$ is the half-width of the peak. Each experiment is repeated three to five times with a plate count reproducibility of 5–8% in relative standard deviation, unless otherwise stated.

In both the anionic and cationic solute cases, the maximum plate count observed is greater than that obtained in a single-capillary experiment; however, the anionic solute and cationic solute in behave differently. For the anionic solute case, a sharp maximum is observed as the voltage applied to the pump capillary 28 is varied, with the maximum corresponding to a field strength on the pump capillary 28 greater than that in the separation capillary 20. In contrast, for the cationic solute case, the plate counts reach a plateau with decreasing field strength on the pump capillary and, further, the field strength corresponding to the plateau region is lower than that in the separation capillary. For a neutral solute a significant increase in plate counts was not observed as a function of auxiliary pumping at any voltage; instead, the plate count decreased as the field strength on the pump capillary 28 was made significantly different (in either direction) from that on the separation capillary 20.

The greater plate counts obtained with an optimum amount of auxiliary electroosmotic pumping relative to the single-capillary case is independent of the degree to which the mobility of the solute and the carrier electrolyte is matched. For the anionic dyes, a borate electrolyte is not optimum because the carrier has a much higher mobility. Significantly greater plate counts are obtained when the principal charge carrier is of slower mobility, for example, when an electrolyte composed of 10 mM anthraquinone-2-sulfonate and 5 mM $Na_2B_4O_7$ is used. Nevertheless, even in this case, a further significant increase in plate counts could be observed with an optimum amount of electroosmotic pumping.

What is claimed is:

1. An apparatus for capillary electrophoresis, comprising:
    (a) a first high voltage source;
    (b) a first electrode being in electrical communication with the first high voltage source;
    (c) a separation capillary containing a sample, the separation capillary having an inlet end and an outlet end, the inlet end being in electrical communication with the first electrode when the separation capillary is filled with an electrolyte solution which is in contact with the first electrode;
    (d) a detector in fluid communication with the outlet end of the separation capillary;
    (e) a grounding joint in fluid communication with the detector
    (f) a pumping capillary having a first end and a second end, the first end being in fluid communication with the grounding joint;
    (g) a second electrode being in electrical communication with the second end of the pumping capillary when the pumping capillary is filled with an electrolyte solution which is in contact with the second electrode; and
    (h) a second high voltage source being in electrical communication with the second electrode.

* * * * *